(12) United States Patent
Paunescu

(10) Patent No.: US 11,662,304 B2
(45) Date of Patent: May 30, 2023

(54) SYSTEM AND METHOD FOR IN SITU MEASURING AND COLLECTING SAMPLES OF ANALYTE CONCENTRATION IN BODILY FLUIDS

(71) Applicant: Johnson & Johnson Consumer Inc., Skillman, NJ (US)

(72) Inventor: Alexandru Paunescu, Clinton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 17/447,947

(22) Filed: Sep. 17, 2021

(65) Prior Publication Data

US 2023/0087775 A1    Mar. 23, 2023

(51) Int. Cl.
*G01N 21/31* (2006.01)
*G01N 33/487* (2006.01)
(Continued)

(52) U.S. Cl.
CPC ........... *G01N 21/31* (2013.01); *G01N 27/223* (2013.01); *G01N 33/487* (2013.01);
(Continued)

(58) Field of Classification Search
CPC .... G01N 27/223; G01N 33/487; A61F 13/42; A61F 13/15585; A61F 13/49
See application file for complete search history.

(56) References Cited

U.S. PATENT DOCUMENTS

| 3,918,433 A | 11/1975 | Fuisz |
| 4,700,714 A | 10/1987 | Fuisz |

(Continued)

FOREIGN PATENT DOCUMENTS

| EP | 1779119 A | 5/2007 |
| WO | WO 2006/023678 A | 3/2006 |

(Continued)

OTHER PUBLICATIONS

U.S. Appl. No. 17/205,460, filed Mar. 18, 2021 Johnson & Johnson Consumer Inc.

(Continued)

*Primary Examiner* — Maurice C Smith

(57) ABSTRACT

A system and related methods include a durable component, an indicator component including an indicator zone comprising at least one colorimetric analyte sensing element, at least one moisture sensor, and a fluid collection reservoir. The durable component contains at least one spectrophotometer, a computing system, and means for electronic communication between the computing system and at least one external device. The indicator component includes at least one colorimetric analyte sensing element and a fluid transport layer in fluid communication with the indicator zone, and it is arranged and configured for attachment to the durable component. In addition, the moisture sensor is arranged and configured to communicate the presence of moisture to initiate a predetermined delay in measuring the concentration of at least one analyte. The fluid collection reservoir is releasable from at least one of the indicator components and the durable component at a predetermined breaking point for clinical analysis.

20 Claims, 8 Drawing Sheets

(51) Int. Cl.
*G01N 27/22* (2006.01)
*G01N 33/52* (2006.01)
*A61F 13/49* (2006.01)
*A61F 13/15* (2006.01)

(52) U.S. Cl.
CPC ............ *G01N 33/528* (2013.01); *A61F 13/15* (2013.01); *A61F 13/15585* (2013.01); *A61F 13/49* (2013.01); *G01N 2201/062* (2013.01)

(56) References Cited

U.S. PATENT DOCUMENTS

| | | | |
|---|---|---|---|
| 6,203,496 B1 * | 3/2001 | Gael | G01N 33/528 604/362 |
| 6,342,037 B1 | 1/2002 | Roe et al. | |
| 8,105,552 B2 | 1/2012 | Xiao et al. | |
| 8,273,939 B2 | 9/2012 | Klofta et al. | |
| 8,293,967 B2 | 10/2012 | Klofta et al. | |
| 9,131,893 B2 | 9/2015 | Faybishenko et al. | |
| 9,820,891 B2 | 11/2017 | Abir | |
| 10,028,701 B2 | 7/2018 | Linton et al. | |
| 10,251,602 B2 | 4/2019 | Faybishenko et al. | |
| 10,285,871 B2 | 5/2019 | Arizti et al. | |
| 10,285,872 B2 | 5/2019 | Arizti et al. | |
| 10,292,112 B2 | 5/2019 | LaVon et al. | |
| 10,462,750 B2 | 10/2019 | LaVon et al. | |
| 10,492,148 B2 | 11/2019 | LaVon et al. | |
| 10,950,340 B2 | 3/2021 | Ranta et al. | |
| 2004/0220538 A1 | 11/2004 | Panopoulos | |
| 2008/0058740 A1 | 3/2008 | Sullivan et al. | |
| 2008/0266117 A1 | 10/2008 | Song et al. | |
| 2010/0100008 A1 | 4/2010 | Chciuk et al. | |
| 2013/0296739 A1 | 11/2013 | Schultz | |
| 2014/0198203 A1 | 7/2014 | Vardi et al. | |
| 2014/0200538 A1 * | 7/2014 | Euliano | A61F 13/42 604/361 |
| 2014/0358099 A1 * | 12/2014 | Durgin | A61F 13/42 340/573.5 |
| 2016/0078176 A1 | 3/2016 | Ranta et al. | |
| 2017/0252225 A1 | 9/2017 | Arizti et al. | |
| 2018/0093475 A1 * | 4/2018 | Strasemeier | A61F 13/15585 |
| 2018/0149635 A1 * | 5/2018 | Abir | A61F 13/42 |
| 2019/0133524 A1 | 5/2019 | Dong et al. | |
| 2020/0206044 A1 | 7/2020 | LaVon et al. | |
| 2020/0222252 A1 | 7/2020 | LaVon et al. | |

FOREIGN PATENT DOCUMENTS

| | | |
|---|---|---|
| WO | WO 2007/073139 A | 6/2007 |
| WO | WO 2017/178417 A | 10/2017 |
| WO | WO 2019/051118 A | 3/2019 |

OTHER PUBLICATIONS

U.S. Appl. No. 17/205,473, filed Mar. 18, 2021 Johnson & Johnson Consumer Inc.
U.S. Appl. No. 17/205,491, filed Mar. 18, 2021 Johnson & Johnson Consumer Inc.
International search report and written opinion dated May 30, 2022, for corresponding international application PCT/US2021/071511.

* cited by examiner

SYSTEM AND METHOD FOR IN SITU MEASURING AND COLLECTING SAMPLES OF ANALYTE CONCENTRATION IN BODILY FLUIDS

BACKGROUND OF THE INVENTION

Field of the Invention

The present invention relates to systems which measure changes in the concentration of analytes in bodily fluids in situ while simultaneously collecting samples for later analysis. More particularly, this invention relates to systems which are used to measure the concentration of analytes in urine over time and methods to measure these analytes and detect early onset disease states in the human body. These systems have a reservoir to simultaneously collect the bodily fluids for subsequent analysis to confirm the in situ analysis and/or to facilitate clinical studies.

Description of Related Art

The analytes found in bodily fluids such as urine or sweat potentially carries evidence of developing local and/or systemic health problems. There is a desire for people in and out of the medical establishment to track and analyze changes in the concentration of analytes in bodily fluids over time.

Currently, people and physicians rely on visible symptoms to diagnose systemic metabolic problems. This often prompts physicians to do urine analysis or blood tests to determine presence or concentrations of various analytes in these bodily fluids. So, in today's practice, a test such as urine analysis is most often used to confirm symptom-based diagnosis, rather than as initial identification of disease. Some conditions, like diabetic ketoacidosis, show visible symptoms only when a person's condition may already warrant an emergency visit to a physician. Other conditions, like urinary tract infection, may not show visible symptoms and result in renal scarring, which may not manifest itself in health problems until many years later.

Non-invasively measuring the analyte concentration in urine content is also ideally suited for epidemiological studies to rapidly identify problems prevalent in specific geographies. Difficulty of sample collection, however, prevents acceleration of research in this area.

Most absorbent articles equipped with sensors, such as diapers, have embedded sensors that are only capable of detecting wetness with some of them capable to qualitatively assess the presence of biomarkers. Often, they transmit that information to a receiving system. The receiving system then alerts a caregiver of a one-time event. These wetness detection systems do not perform a diagnosis.

An example, U.S. Ser. No. 10/462,750B2 purports to disclose a diaper that reports the presence of a targeted biomarker. Unfortunately, the qualitative report of the biomarker cannot determine the concentration of that biomarker—a measurement of significant value in clinical studies and in diagnosis.

Some existing diagnostic systems rely on urinalysis strips being dipped into a urine sample and are manually or automatically read by an imaging device or cell phone. Other diagnostic systems rely on urinalysis strips mounted to the exterior surface of an absorbent article, and, once wet, are manually or automatically read by an imaging device or cell phone. In either case, data from present readings can be compared with those of both past and future readings.

In either approach, the reading of the urinalysis strips is performed at a point in time after the strips have become wet with urine. Many of the chemicals used in the test strips are sensitive to time, temperature, degree of wetness, etc. of exposure. So, accurate and repeatable readings are difficult to obtain. These systems also lack the ability to corroborate the readings determined with analyte readings determined by laboratory procedures. Accuracy and repeatability are critical for tracing changes in analyte concentrations over time.

In summary, analytes found in bodily fluid may evidence of developing local and/or systemic health problems. There is a desire to track and analyze changes in the concentration of analytes in bodily fluids such as urine over time. However, for the data to be valuable, the readings must be accurate and repeatable.

In addition to in situ analysis of bodily fluids using test strips and kits described above, clinical studies and clinical analysis employ collection of bodily fluid samples for subsequent analysis in professional laboratories capable of screening a broader panel of molecular biomarkers. Unfortunately, simultaneous collection of samples for laboratory analysis and accurate in situ analysis of the same bodily fluids is not possible. Therefore, determination of the accuracy of an in situ testing system requires a comparison of two clouds of data—one of clinical data and the other of the in situ data.

Therefore, what is needed is a system that can provide accurate, immediate, in situ bodily fluid analysis and permit simultaneous collection of the same bodily fluid for subsequent analysis of a broader panel of molecular biomarkers.

BRIEF SUMMARY OF THE INVENTION

I have invented a system that combines an easy-to-use device capable of delivering accurate in situ analysis of bodily fluids for use by at-home caregivers that is sufficiently accurate for clinical trials with a simultaneous sample collection for confirmation or expanding the size of the panel for more in-depth insight of such in situ analysis.

The system includes a durable component, an indicator component including an indicator zone comprising at least one colorimetric analyte sensing element, at least one moisture sensor, and a fluid collection reservoir. The durable component has a housing having at least one window and contains at least one spectrophotometer adjacent to and optically communicating with the window, a computing system having at least one processor and data storage, and means for electronic communication between the computing system and at least one external device. The indicator component includes at least one colorimetric analyte sensing element and a fluid transport layer in fluid communication with the indicator zone, and it is arranged and configured for attachment to the durable component while the indicator zone is disposed adjacent to and in optical communication with the at least one window and the at least one spectrophotometer, and the computing system is operatively connected to the moisture sensor and the at least one spectrophotometer. In addition, the moisture sensor is arranged and configured to communicate the presence of moisture in the colorimetric analyte sensing element to the computing system; and each of the at least one colorimetric analyte sensing elements is associated with a spectrophotometer. The fluid collection reservoir has fluid impervious walls and a port in fluid communication with the fluid transport layer, and it is releasable from at least one of the indicator components and the durable component at a predetermined breaking point.

A novel and useful method of measuring analyte concentration in a bodily fluid includes the steps of collecting and transporting bodily fluid to at least one colorimetric analyte sensing element and at least one fluid collection reservoir, which colorimetric analyte sensing element detects the presence of bodily fluid in contact with the at least one colorimetric analyte sensing element. Additional steps include collecting optical data relating to the at least one colorimetric analyte sensing element with at least one spectrophotometer after a predetermined time period after detecting the presence of bodily fluid in contact with the colorimetric analyte sensing element, communicating the optical data to a computing system having at least one processor and data storage, and analyzing the optical data to determine at least one analyte concentration in the bodily fluid. In addition, the method includes the step of sealing the fluid collection reservoir for transport of the sealed fluid collection reservoir to a laboratory for laboratory analysis of the at least one analyte concentration.

Another novel and useful method of measuring analyte concentration in a bodily fluid. The method includes the steps of obtaining a durable component, removing an indicator component from an individual package, and coupling the indicator component to the durable component. The indicator component includes a transport layer, an indicator zone comprising at least one colorimetric analyte sensing element, and a fluid collection reservoir having fluid impervious walls and a port in fluid communication with the fluid transport layer. The fluid collection reservoir is releasable from the indicator component at a predetermined breaking point. The durable component has a housing having at least one window and contains at least one spectrophotometer adjacent to and optically communicating with the window, a computing system having at least one processor and data storage, means for electronic communication between the computing system and at least one external device, and at least one moisture sensor. The indicator zone is disposed adjacent to and in optical communication with the at least one window and the at least one spectrophotometer, and the computing system is operatively connected to the moisture sensor and the at least one spectrophotometer. The moisture sensor is disposed adjacent the indicator zone, each of the at least one colorimetric analyte sensing element is associated with a spectrophotometer. The method also includes the steps of placing the assembled device in contact with a source of the bodily fluid, collecting and transporting the bodily fluid to the at least one colorimetric analyte sensing element, and detecting the presence of the bodily fluid in contact with the at least one colorimetric analyte sensing element. The method further includes the steps of collecting optical data relating to the at least one colorimetric analyte sensing element with at least one spectrophotometer after a predetermined time period after detecting the presence of bodily fluid in contact with the colorimetric analyte sensing element, communicating the optical data to a computing system having at least one processor and data storage, and analyzing the optical data to determine at least one analyte concentration in the bodily fluid. The method also includes removing the fluid collection reservoir from the indicator component and sealing the fluid collection reservoir port for transport of the sealed fluid collection reservoir to a laboratory for laboratory analysis of the at least one analyte concentration.

DETAILED DESCRIPTION OF THE INVENTION

Figure 1:
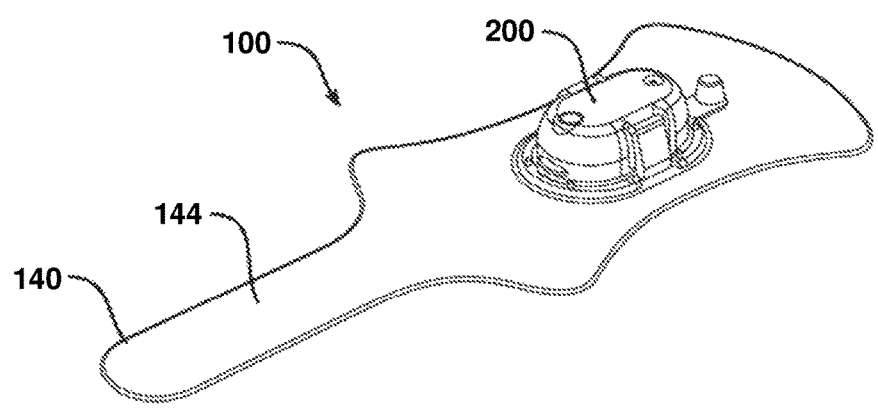
FIG. 1 is a bottom perspective view of a system for measuring analyte concentration and sample collection of the present invention.

The present invention relates to systems for use in absorbent articles for in situ measurement of the concentration of analytes in bodily fluids that permits the monitoring of such analytes in bodily fluids such as urine over time, and methods for using the system to measure the concentration of analytes in bodily fluids over time, as well as methods to use these analyte measurements over time to detect early onset disease states in the human body. These systems include a reservoir to simultaneously collect the bodily fluids to confirm the in situ analysis.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

As used in the specification and the claims, the terms "panel" or "test panel" and variants thereof relate to a predetermined group of medical tests or analyses used an aid in the diagnosis and treatment of disease.

The present invention relates to systems and methods to enable monitoring of analyte concentration in an absorbent article. The systems and methods also allow statistical analysis and determination of changes in the health state by the collection of multiple data points over time, which may be evidence of developing metabolic system problems. Other data such as medical and family history as well as current variables such as age, temperature, and/or other current markers may be used to supplement trend and statistical analysis.

The apparatus or system for collecting samples of and measuring analyte concentration in bodily fluids may be associated with an absorbent article. The system has an indicator component and a durable component. The indicator component includes an indicator zone that has a colorimetric analyte sensing element which may be disposed in an optional flexible web, a fluid transport layer, an optional first flexible web, an optional top plate, a coupler which may be a holding plate, an adhesive layer, and a fluid collection reservoir. The indicator component is preferably disposable.

The colorimetric analyte sensing element has perforations and is disposed in the aperture of the second flexible web. The colorimetric analyte sensing element may be a reagent impregnated matrix designed to produce a visual indication of the presence of a preselected analyte in sample produced by the wearer of the system. The preselected analyte measured by system may be glucose, ketone, bilirubin, blood, pH, protein, urobilinogen, nitrite, leukocytes, and/or creatinine, among others.

For example, the absorbent article may be a diaper, the fluid being tested may be urine and the preselected analyte measured by the apparatus or system for measuring analyte concentration may be glucose. Glycosuria, or glucose in the urine, is the presence of higher-than-normal levels of sugar in the urine and may be due to complications with one's kidneys or diabetes. Some of the most common causes of glucose in the urine include: diabetes mellitus, hyperthyroidism, benign glycosuria, liver cirrhosis, or a high sugar diet. Biosensor(s) capable of converting a preferred biomarker into a calorimetrically readable result could be used in genomics, transcriptomics, metabolomics and proteomics as well to determine the presence of inflammatory biomarkers that are present in urine may be used in the inventive system.

As mentioned, colorimetric analyte sensing element, disposed in the opening of the second flexible web is in fluid communication with the fluid transport layer. The fluid transport layer, in turn, is in fluid communication with the first flexible web. The second flexible web has a first side, and is made of non-absorbing material, such as a polyethylene foam. The fluid transport layer has a first side, and perforations, and is made of wicking material, such as fabric or paper, that is effective in spreading and transporting fluid via capillary action. The first flexible web has a first side, and perforations, and is made of a non-absorbing apertured film, such as a polyethylene mesh.

The second flexible web, the fluid transport layer, and the first flexible web are designed to aid in the transport of fluid to the colorimetric analyte sensing element. In use, fluid from the absorbable article first contacts the first side of the first flexible web. Since the first flexible web is a non-absorbing apertured film, fluid passes through the first flexible web and contacts the first side of the fluid transport layer. The fluid then permeates throughout the fluid transport layer. The fluid will contact the first side of the second flexible web. But, since the second flexible web is made of non-absorbing material, fluid in the transport layer does not penetrate the second flexible web. Finally, the fluid in the transport layer comes into contact with the colorimetric analyte sensing element.

The sensing element disposed in the second flexible web, the fluid transport layer, and the first flexible web are stacked, and are held together by the top plate and the holding plate. The holding plate has pins. The pins sequentially pass through the perforations of the colorimetric analyte sensing element, the perforations of the fluid transport layer, and the perforations of the first flexible web. Though not shown, the top plate has blind holes in which the pins are disposed. A friction fit between the top plate blind holes and the pins hold the components of the indicator component together. Alternative assemblies may be held together by other interactions, such as snap fit, ultrasonic weld, heat weld, other mechanical fasteners, and the like.

The top plate and holding plate are arranged and configured to provide a predetermined spacing to accommodate indicator component layers with predetermined fluid transport capacity to the indicator zone. This provides a more controlled delivery of bodily fluid to the indicator zone and the associated timing between the bodily fluid arriving at the indicator zone and the colorimetric measurement, described in more detail, below.

The top plate may have channels on the side facing the first side of the first flexible web. The channels may help direct fluid from the absorbent article to the first side of the first flexible web.

The durable component has a housing with a window. A spectrophotometer is disposed in the housing. The components of the spectrophotometer include light sources and photodetectors. The spectrophotometer is adjacent to and in optical communication with the window in the housing. This allows the spectrophotometer to be in optical communication with the colorimetric analyte sensing element of the indicator component.

The spectrophotometer may include at least two or more light sources and at least two photodetectors, for example, or at least four or more light sources and at least four or more photodetectors.

A male connector protrusion surrounding the window on the housing allows the durable component to be releasably attached to the indicator component. The durable component of the system for measuring analyte concentration in an absorbent article has conductive strips disposed on the top surface of the male connector protrusion which act as a moisture sensor, arranged and configured to communicate the presence of moisture in the colorimetric analyte sensing element to the computing system disposed in the durable component.

The light sources and the photodetectors may be linearly arranged and evenly spaced in the housing of the system for measuring analyte concentration in an absorbent article, and are typically located on a printed circuit board (PCB). The PCB mechanically supports and electrically connects electronic components using conductive tracks, pads and other features etched from copper sheets laminated onto a non-conductive substrate. Components (e.g., capacitors, resistors, controllers, power sources, light sources, detectors) are generally soldered on the PCB. The PCB can be supported within the housing of the durable component by means of support brackets, or may be attached directly to the inner surface of the housing.

The PCB has a computing system having one or more processors and a memory, as well as means for electronic communication to send the results of analyses to data processing systems that are external to the system for measuring analyte concentration in an absorbent article. Data processing systems that may be used include at least one external device including server computers, client computers, and handheld devices such as cellphones.

The light source and photodetector components of the test spectrophotometer are disposed on the surface of the PCB. They may be shielded from ambient light by panels or shields. Skirts may be attached to the surface of the PCB to optically isolate the photodetectors from the light sources. So, in operation, light which emanates from the light sources cannot impinge on photodetector without having reflected off the colorimetric analyte sensing element.

Alternatively, lenses can be placed over the light sources so that in operation light which emanates from the light sources cannot impinge on the photodetectors without having reflected off the colorimetric analyte sensing element. Potting materials can also be used to focus the light from the light sources at the colorimetric analyte sensing element.

The light sources may be light-emitting diodes (LEDs), a semiconductor light source that emits light when current flows through it. LEDs have many advantages over incandescent light sources, including lower energy consumption, longer lifetime, improved physical robustness, smaller size, and faster switching. The light sources may be RGB LEDs. Mixing red, green, and blue sources can produce white light with proper blending of the colors. In addition, the colors emanating from RGB LEDs may be monochromatic, allowing data to be obtained in narrow wavelength regions.

The photodetectors are also called photosensors. Photodetectors are sensors of light or other electromagnetic radiation. A photodetector has a p-n junction that converts light photons into current. The absorbed photons make electron—hole pairs in the depletion region. Certain photodetectors can measure the amount of white light received.

Other photodetectors specifically measure the red, green, and blue light, allowing data to be obtained in narrow wavelength regions. In a system employing red, green, and blue light, the sources may emit light in narrow red, green, and blue wavelengths. The emitted light waves reflect off the colorimetric analyte sensing element. The photodectors measure reflected light. A sequential emission of red light, green light, and blue light allows for the near simultaneous collection of three data points. Alternatively, the sequence of emitted red light, green light, and blue light may vary.

The components of the spectrophotometer may be coated with a protective material. The protective material keeps the moisture from the colorimetric analyte sensing element from contacting, and potentially damaging, the components of the spectrophotometer.

The indicator components are arranged and configured for releasable attachment to the durable component. When assembled, the colorimetric analyte sensing elements are disposed adjacent to and in optical communication with the window and the elements of the spectrophotometer.

Conductive strips are disposed on the top surface of the male connector protrusion of the housing of the system for measuring analyte concentration in an absorbent article. The conductive strips act as a moisture sensor in the system and are arranged and configured to communicate the presence of moisture in the colorimetric analyte sensing element to the computing system disposed in the durable component. In turn, the computing system disposed in the durable component is operatively connected to the moisture sensor and the components of the spectrophotometer. The function of the conductive strips in the moisture sensor will be described later.

The moisture sensing system described above allows the spectrophotometer to perform its reading of the emitted light waves reflect off the colorimetric analyte sensing element at a point in time after the strips have become wet with moisture. This solves the issue of chemicals used in the test strips are sensitive to time, temperature, and degree of wetness, allowing accurate and repeatable readings are to be obtained.

Using four narrow beam LEDs spaced about the photodetectors. Therefore, the onset of wetness can be detected by a change of impedance by the conductive strips, and for example, four narrow beam LEDs can be spaced about the photodetectors. The accuracy of the beginning of sufficient saturation of the colorimetric analyte sensing element can be improved by sequentially activating each of the narrow beam LEDs and comparing the light detected by the photodetectors. If there is a significant difference among the data returned by the photodetector as a result of different narrow beam LEDs, the colorimetric analyte sensing element may not be sufficiently saturated for reliable analysis. Therefore, the system may begin collecting optical data relating to the colorimetric analyte sensing element after a predetermined time period following bodily fluid contact with the colorimetric analyte sensing element as determined by (1) a change of impedance by the conductive strips, and (2) relatively consistent data returned by the photodetector as a result of different narrow beam LEDs indicating substantially uniform wetness of the colorimetric analyte sensing element.

Although while the description above refers to a system for measuring analyte concentration in an absorbent article which has an indicator component and a durable component, it is envisioned that in some cases the durable component can be combined with a plurality of indicator components to create a kit for measuring analyte concentration in an absorbent article. The kit has at least one, preferably one or more, individually packaged indicator components. This allows for the kit to measure analyte concentration in an absorbent article daily, or weekly, or monthly, or one or more times a day, or week or month. When used in this manner, the system is used to track changes in measured analyte concentration over the course of days, week, months, or even years.

Disposable absorbent articles for use in the system for measuring analyte concentrations include absorbent hygiene articles such as diapers (including infant diapers, training pants and adult incontinence products) and pads (including feminine sanitary napkins and pantiliners and nursing pads).

For example, an absorbent article for use in the system for measuring analyte concentrations is a diaper, and analyte concentrations are being measured in urine. The indicator component has attachment means such as an adhesive layer. The adhesive layer is used to attach, or couple, the indicator component of the system to the fluid transport layer of the diaper. The system may be attached to a body-facing surface of the diaper. Other attachment means will be readily apparent, including without limitation, mechanical fasteners, such as clips, clamps, hook-and-loop systems, and bands; magnetic (including static electricity); friction; and the like. Indicator component may be arranged and configured for releasable attachment to a diaper.

As discussed above, the system for measuring analyte concentration in an absorbent article uses colorimetric analyte sensing elements to produce a visual indication of the presence of preselected analytes in samples freshly produced by the wearer of system. The system also has a means for collecting fluid for later analysis. The holding plate of indicator component has a fluid collection reservoir attached thereto by reservoir connector. The fluid collection reservoir may comprise an absorbent material, such as a sponge, to collect bodily fluid, such as urine. Sponges impregnated with boric acid and sodium formate (urine preservatives), such as the UNISPONGE, trademarked by COPAN Diagnostics (Murrieta, Calif.) may be used. Other urine absorbent materials include woven or non-woven fibers of natural or synthetic materials, or absorbent gels. Superabsorbent polymers (SAPs) such as HYSORB SAPs from BASF (Ludwigshafen, DE).

The fluid collected by the fluid collection reservoir may be sent to a comprehensive testing site for confirmation to compare the concentrations determined by the colorimetric analyte sensing elements to concentrations determined by "gold standard" test methods to confirm the in situ analysis. Tests may also be run on an expanded panel for more in-depth insight of such in situ analysis, i.e., for other analytes not measured by the colorimetric analyte sensing elements to give a more comprehensive determination of user health.

Fluid collection reservoir includes a sealable container body for receiving the bodily fluid, and a port through which the bodily fluid enters the reservoir. The container body has liquid impervious walls, and is made of a rigid, or semi-rigid material, such as elastomeric plastics. The port may have a one-way valve allowing the bodily fluid to enter the reservoir.

The fluid collection reservoir is in fluid communication with the fluid transport layer, and may contain an absorbent material, such as the sponges, woven fabrics, non-woven fabrics, or absorbent gels described above. The absorbent material contained within the fluid collection reservoir is capable of drawing bodily fluids from the fluid transport layer. Drawing of bodily fluids from the fluid transport layer to the reservoir may be accomplished by capillary gradient to draw the sample of bodily fluid into the reservoir.

The fluid collection reservoir is detachable from the indicator component at a predetermined breaking point. The reservoir is sealable so that it can be capped upon separation from the indicator component. Sealing of the fluid container reservoir may include a flip top, snap top, or screw top to close and seal the container.

Fluid collection reservoir may be disposed in an opening of a reservoir retriever on the durable component. When the durable component is detached from the holding plate, the reservoir retriever may detach the fluid collection reservoir from the holding plate. A twist-off feature can be included to aid in the removal of the fluid collection reservoir from the holding plate.

The presently disclosed subject matter will now be described more fully hereinafter with reference to the accompanying drawings and examples. The presently disclosed subject matter can, however, be embodied in different forms and should not be construed as limited to any specific examples set forth herein and is to be accorded the widest scope consistent with the features described herein. Rather, any specific examples are provided so that this disclosure will be thorough and complete and will fully convey the scope of the invention to those skilled in the art to which the invention belongs. It is believed that one skilled in the art can, based upon the description herein, utilize the present invention to its fullest extent.

Figure 2:
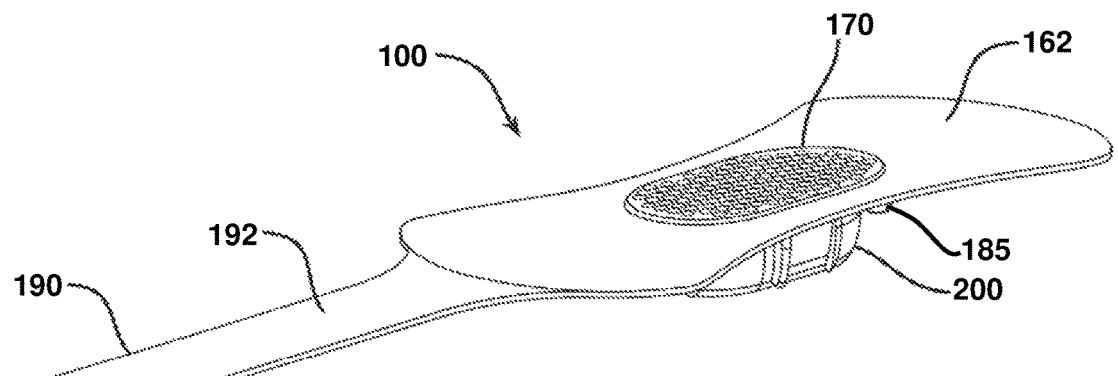
FIG. 2 is a top perspective view of the system for measuring analyte concentration and sample collection of FIG. 1.

The system for measuring analyte concentration in an absorbent article may have a plurality of colorimetric analyte sensing elements. FIGS. 1 and 2 show a system for measuring analyte concentration in an absorbent article of the present invention. System 100 has an indicator component 120 and a durable component 200. FIGS. 1 and 2 are top and bottom perspective views, respectively, of system 100 when full assembled.

Figure 3:
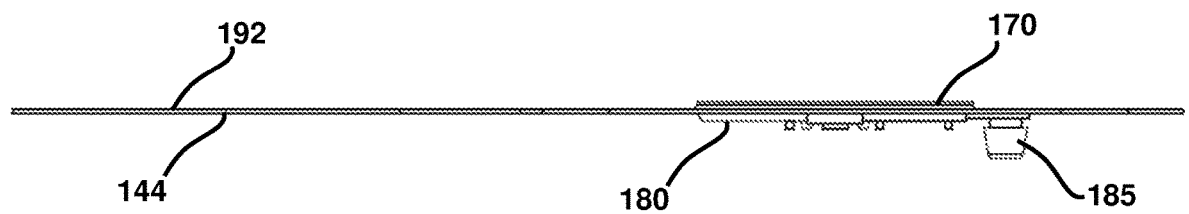
FIG. 3 is a side view of the indicator and sample collection component of the system of FIG. 1.
Figure 4:
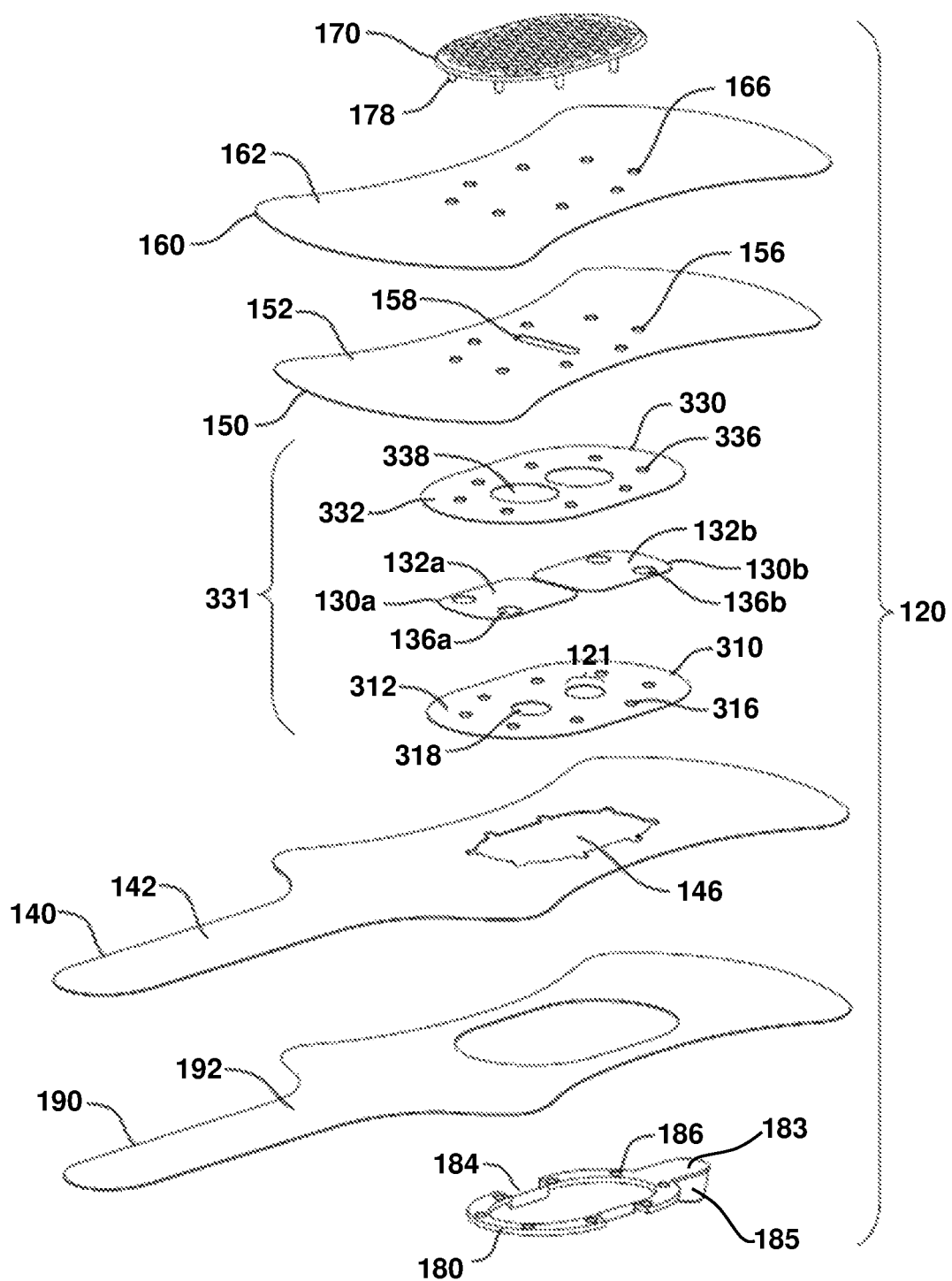
FIG. 4 is an exploded top perspective view of the indicator and sample collection component of the system of FIGS. 1 to 3.

Indicator component 120 is shown in a side view in FIG. 3, and in an exploded view in FIG. 4. Indicator component 120 includes an indicator zone 121 that has a pair of colorimetric analyte sensing elements, first colorimetric analyte sensing element 130a, and second colorimetric analyte sensing element 130b. First colorimetric analyte sensing element 130a has a first side 132a and a second side 134a, as well as perforations 136a. Second colorimetric analyte sensing element 130b has a first side 132b and a second side 134b, as well as perforations 136b.

Colorimetric analyte sensing elements 130a, 130b may be reagent impregnated matrices designed to produce a visual indication of the presence of a preselected analyte in sample produced by the wearer of system 100. Chemistries and methods of detecting analytes by producing a visual indication are well known in the art. The preselected analyte measured by system 100 may be, glucose, ketones, bilirubin, blood, pH, protein, urobilinogen, nitrite, leukocytes, and/or creatinine, among others.

Colorimetric analyte sensing elements 130a, 130b may be designed to produce a visual indication of the presence of the same preselected analyte in sample produced by the wearer of system 100. In this case, colorimetric analyte sensing elements 130a, 130b act to confirm the analysis. Colorimetric analyte sensing elements 130a, 130b may also be designed to produce a visual indication of the presence of different preselected analytes in sample produced by the wearer of system 100.

Again, the absorbent article may be a diaper, the fluid being tested is urine and the preselected analyte measured by system 100 is glucose. Glycosuria, or glucose in the urine, is the presence of higher-than-normal levels of sugar in the urine and may be due to complications with one's kidneys or diabetes.

The preselected analytes measured by system 100 may also be ketones. If cells in the body do not get sufficient glucose, the body burns fat for energy instead. This produces ketones which can show up in the blood and urine. High ketone levels in urine may indicate diabetic ketoacidosis (DKA), a complication that can lead to a coma or even death.

Some of the most common causes of glucose or ketones in the urine include: diabetes mellitus, hyperthyroidism, benign glycosuria, liver cirrhosis, or a high sugar diet. Biosensor(s) capable of converting a preferred biomarker into a calorimetrically readable result could be used in genomics, transcriptomics, metabolomics and proteomics as well to determine the presence of inflammatory biomarkers that are present in urine may be used in the inventive system.

The other components of indicator component 120 include an optional top plate 170, an optional first flexible web 160, a fluid transport layer 150, a second flexible web 140, an adhesive layer 190, and a coupler shown here as holding plate 180.

Colorimetric analyte sensing elements 130a, 130b are encapsulated between first encapsulation layer 310 and second encapsulation layer 330 to form a fluid impervious envelope 331. First encapsulation layer 310 has a first side 312 and a second side 314, as well as perforations 316 and apertures 318. Second encapsulation layer 330 has a first side 332 and a second side 334, as well as perforations 336 and apertures 338.

Figure 5:
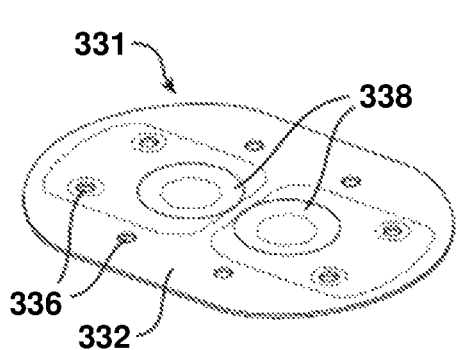
FIG. 5 is a top perspective view of the fluid impervious envelope encapsulating colorimetric analyte sensing elements of the indicator and sample collection component of FIG. 4.
Figure 6:
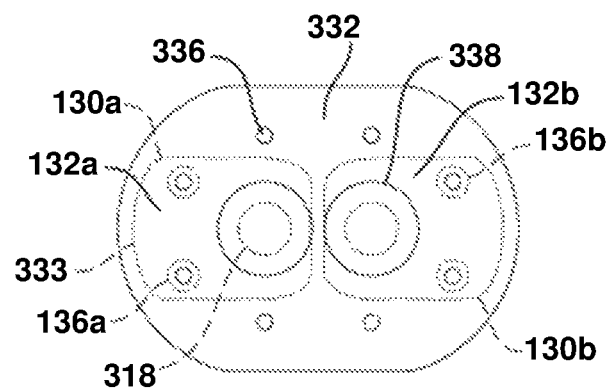
FIG. 6 is a top view of the fluid impervious envelope encapsulating colorimetric analyte sensing elements of the indicator and sample collection component FIG. 4.

FIG. 5 is a top perspective view of the fluid impervious envelope 331 encapsulating colorimetric analyte sensing elements 130a, 130b of indicator component 120 of system 100. FIG. 6 shows a top view of the fluid impervious envelope 331 encapsulating colorimetric analyte sensing elements of FIG. 5. The figures show, in solid lines, first side 332, perforations 336 and aperture 338 of second encapsulation layer 330. In dashed lines, the figures show colorimetric analyte sensing elements 130a, 130b, their first sides 132a, 132b and perforations 136a, 136b as well as apertures 318 of first encapsulation layer 310. The dashed lines showing colorimetric analyte sensing elements 130a, 130b, also outline discrete pockets 333 (one of two shown in FIG. 6) formed when first encapsulation layer 310 and second encapsulation layer 330 are sealed together where their surfaces contact.

When assembled, first perforations 336 of second encapsulation layer 330 are in alignment with perforations 136a, 136b of colorimetric analyte sensing elements 130a, 130b, as well as perforations 316 of first encapsulation layer 310 (not shown). In addition, apertures 338 of second encapsulation layer 330 are in alignment with apertures 318 of first encapsulation layer 310.

Figure 7:
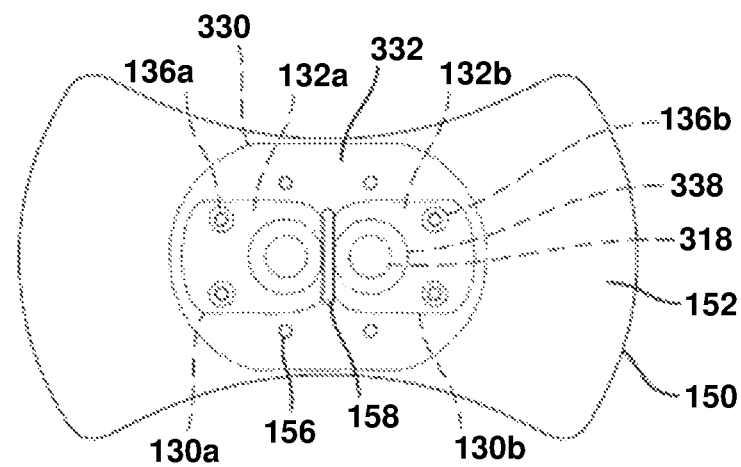
FIG. 7 is a top view of partially assembled indicator and sample collection component of FIG. 4.

The fluid impervious envelope 331 encapsulating colorimetric analyte sensing elements 130a, 130b of indicator component 120 of system 100 is disposed on fluid transport layer 150. This partially assembled indicator component of the system 100 is shown in a top in view FIG. 7, and in bottom view in FIG. 8. FIG. 7 shows, in solid lines, first side 152, first perforations 156 and second perforation 158 of fluid transport layer 150. In dashed lines, the figures show colorimetric analyte sensing elements 130a, 130b, their first sides 132a, 132b and perforations 136a, 136b, as well as apertures 318 of first encapsulation layer 310 and first side 332 and apertures 338 of second encapsulation layer 330.

Figure 8:
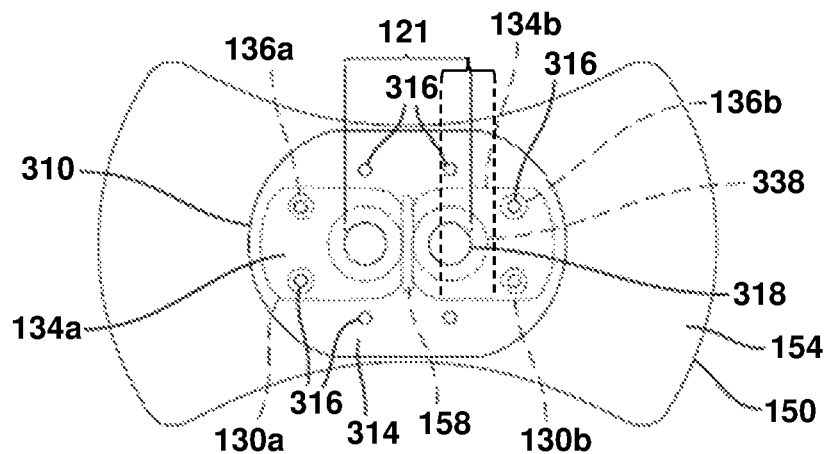
FIG. 8 is a bottom view of partially assembled indicator and sample collection component of the FIG. 4.

FIG. 8 shows, in solid lines, second side 154 of fluid transport layer 150, as well as second side 314, perforations 316 and apertures 318 of first encapsulation layer 310. In dashed lines, the figures show colorimetric analyte sensing elements 130a, 130b, their second sides 134a, 134b and perforations 136a, 136b, and second perforation 158 of fluid transport layer 150.

Second flexible web 140 has a first side 142, a second side 144 and opening 146, and is made of non-absorbing material, such as a polyethylene foam. The fluid impervious envelope 331 encapsulating colorimetric analyte sensing elements 130a, 130b is disposed on second flexible web 140, specifically in opening 146 of second flexible web 140 and is in fluid communication with fluid transport layer 150. Fluid transport layer 150, in turn, is in fluid communication with first flexible web 160. First flexible web 160 has a first side 162, and perforations 166, and is made of a non-absorbing apertured film, such as a polyethylene mesh.

Second flexible web 140, fluid transport layer 150, and first flexible web 160 are designed to control the transport of bodily fluids to the colorimetric analyte sensing elements 130a, 130b and to limit cross-contamination of fluids among different colorimetric analyte sensing elements. In use, fluid from the absorbable article first contacts first side 162 of first flexible web 160. Since first flexible web 160 is a non-absorbing apertured film, fluid passes through first flexible web 160 and contacts first side 152 of fluid transport layer 150. The fluid then permeates throughout fluid transport layer 150. The fluid will contact first side 142 of second flexible web 140. But, since second flexible web 140 is made of non-absorbing material, fluid in fluid transport layer 150 does not penetrate second flexible web 140. Finally, the fluid in transport layer 150 passes through apertures 338 of second encapsulation layer 330 to contact the colorimetric analyte sensing elements 130a, 130b. Cross-contamination between the two colorimetric analyte sensing elements is eliminated or at least made insignificant and not detectable by means of the fluid barrier defined by the gap in capillarity within the fluid transport layer 150 provided by the second perforation 158.

Colorimetric analyte sensing elements 130a, 130b, first encapsulation layer 310, second encapsulation layer 330, second flexible web 140, fluid transport layer 150, and first flexible web 160 are stacked, as shown in FIG. 4, and are held together by top plate 170 and holding plate 180. Top plate 170 has pins 178. Pins 178 sequentially pass through perforations 166 of first flexible web 160, first perforations 156 of fluid transport layer 150, perforations 316 of first encapsulation layer 310, perforations 136a, 136b of colorimetric analyte sensing elements 130a, 130b, first perforations 336 of second encapsulation layer 330, opening 146 of second flexible web 140, and are finally disposed in blind holes 186 of holding plate 180. A friction fit between top plate pins 178 and blind holes 186 hold the components of indicator component 120 together. Alternative assemblies may be held together by other interactions, such as snap fit, ultrasonic weld, heat weld, other mechanical fasteners, and the like.

Top plate 170 may have one or more channels on the side facing first side 162 of first flexible web 160. The channel(s) may help direct fluid from the absorbent article to the first side 162 of first flexible web 160.

Indicator component 120 may have attachment means, such as adhesive layer 190. Adhesive layer 190 has a first side 192 and a second side 194, and is used to attach, or couple, indicator component 120 of system 100 to the fluid transport layer of the absorbent article, such as a diaper.

Figure 9:
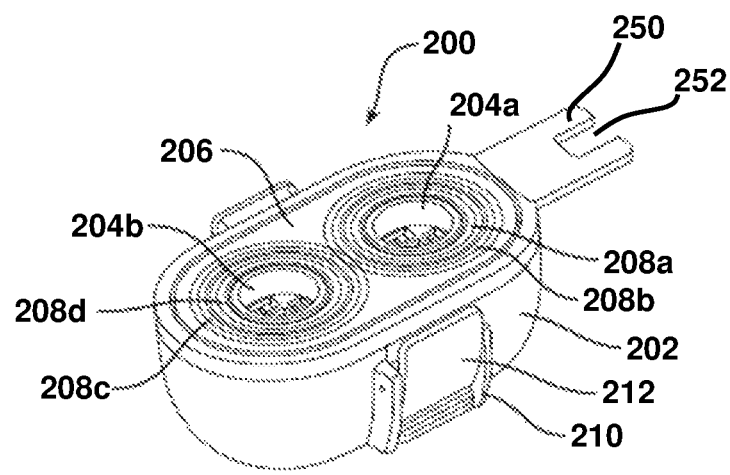
FIG. 9 is a top perspective view the durable component of the system of FIGS. 1 and 2.
Figure 10:
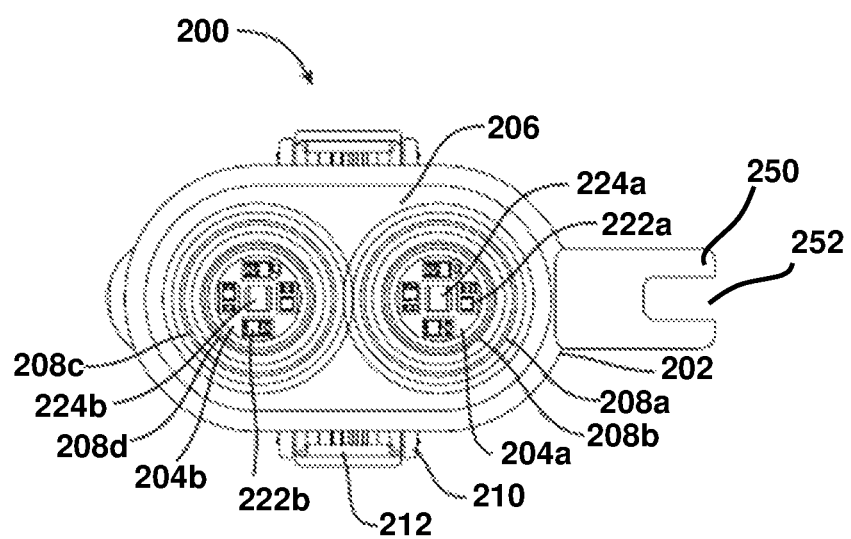
FIG. 10 is a top view of the durable component of the system of FIGS. 1 and 2.

A durable component 200 of the system is shown in top perspective view in FIG. 9, and in top view in FIG. 10. Durable component 200 has a housing 202 with a pair of windows, first window 204a, and second window 204b. Durable component 200 also has a flat top surface 206. A pair of spectrophotometers are disposed in housing 202. The first spectrophotometer is adjacent to and in optical communication with first window 204a. The components of the first spectrophotometer include light sources 222a and photodetector 224a. First spectrophotometer is in optical communication with colorimetric analyte sensing element 130a. The second spectrophotometer is adjacent to and in optical communication with second window 204b. The components of the second spectrophotometer include light sources 222b and photodetector 224b. Second spectrophotometer is in optical communication with colorimetric analyte sensing element 130b. While the durable component 200 has been shown with two spectrophotometers, additional spectrophotometers may be included for measurements of additional analytes or bodily fluid conditions, such as pH, temperature, etc. Indicator zone 121 is the area of indicator component 120 where colorimetric analyte sensing element 130a is exposed to light sources 222a.

Thought not shown, durable component 200 also has a printed circuit board (PCB) with a computing system having one or more processors and a memory, as well as means for electronic communication to send the results of analyses to data processing systems that are external to system 100. Data processing systems that may be used include at least one external device including server computers, client computers, and handheld devices such as cellphones.

As shown in FIGS. 9 and 10, the first and second spectrophotometer may include four light sources 222a, 222b and each spectrophotometer has one photodetector 224a, 224b. Each spectrophotometer may have associated therewith at least one light sources 222a, 222b. Each spectrophotometer may include at least six or more light sources 222a, 222b. As mentioned earlier, light sources 222a, 222b may be light-emitting diodes (LEDs), and more specifically, RGB LEDs. Light sources 222a, 222b may sequentially emit red light, green light, and blue light, allowing for the near simultaneous collection of three data points, or, the sequence of emitted red light, green light, and blue light may vary.

The photodetectors 224a, 224b in the spectrometers, as discussed previously, may specifically measure the red, green, and blue light, allowing data to be obtained in narrow wavelength regions. The light waves emitted from light sources 222a reflect off colorimetric analyte sensing element 130a, and the reflected light is measure by photodetector 224a. The light waves emitted from light sources 222b reflect off colorimetric analyte sensing element 130b, and the reflected light is measure by photodetector 224b. The components of the spectrophotometer may be coated with a protective material. The protective material keeps the moisture from the colorimetric analyte sensing elements 130a, 130b from contacting, and potentially damaging, the components of the spectrophotometers.

FIGS. 9 and 10 also show connectors 210 disposed on housing 202. Connectors 210 comprise standard spring-loaded clips 212 that are biased to hold clips 212 to housing 202 of durable component 200. As shown in FIG. 4, holding plate 180 has receiving elements 184 disposed thereon. To releasably attach durable component 200 to holding plate 180, clips 212 are fastened to receiving elements 184. By this means, durable component 200 is releasably attach to indicator component 120. Other attachment means will be readily apparent, including without limitation, mechanical fasteners, such as clamps, hook-and-loop systems, threaded apertures, bayonet couplings, straps, belts, and bands; magnetic (including static electricity); friction; and the like.

FIGS. 9 and 10 also show reservoir retriever 250 disposed on housing 202 of durable component 200. Reservoir retriever 250 has opening 252 which, as discussed later, is used to retrieve fluid collection reservoir 185 from holding plate 180.

FIG. 10 also shows conductive strips 208a, 208b, 208c and 208d disposed on top surface 206 of durable component 200. Conductive strips 208a, 208b, 208c and 208d act as moisture sensors, arranged and configured to communicate the presence of moisture in colorimetric analyte sensing elements 130a, 130b to the computing system disposed in durable component 200. As shown in FIG. 10, conductive strips 208a and 208b are associated with first window 204a and colorimetric analyte sensing element 130a. Conductive strips 208c and 208d are associated with second window 204b and colorimetric analyte sensing element 130b. The computing system disposed in durable component 200 is operatively connected to the moisture sensors as well as the components of the spectrophotometer.

Conductive strips 208a and 208b are adjacent to colorimetric analyte sensing element 130a. When moisture impinges on colorimetric analyte sensing element 130a, it will also contact portions of conductive strips 208a and 208b. Conductive strips 208c and 208d are adjacent to colorimetric analyte sensing element 130b. When moisture impinges on colorimetric analyte sensing element 130b, it will also contact portions of conductive strips 208c and 208d.

Figure 13:
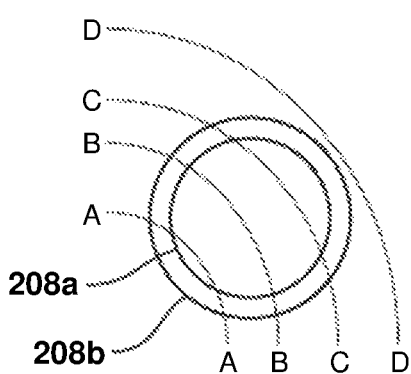
FIG. 13 is a top view of the moisture sensor element of the indicator component of the system for measuring analyte concentration in an absorbent article as a moisture front crosses the element.
Figure 14:
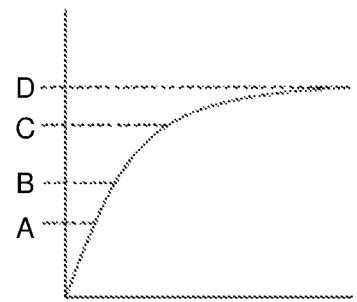
FIG. 14 is a capacitance versus time plot as a moisture front crosses the moisture sensor element of the indicator component of the system for measuring analyte concentration.

FIGS. 13 and 14 describe the function of conductive strips 208a and 208b in the moisture sensor in system 100. Conductive strips 208c and 208d function in the same manner. FIG. 13 is a top view of conductive strips 208a and 208b at several time points during the progression of a moisture front across the strips. The progression of the front is shown as A-A, B-B, C-C and D-D. At time point A-A, the moisture front has progressed partially across conductive strips 208a and 208b. Further progression across strips 208a and 208b are shown as time points B-B and C-C, while D-D shows a time point where the moisture front has fully crossed strips 208a and 208b.

Though capacitance is discussed above, other electrical properties, such as resistance, will also change as the moisture front progresses across strips 208a and 208b.

FIG. 14 shows an example of the change in an electrical property between strips 208a and 208b as the moisture front progresses across the strips. This figure shows a capacitance versus time plot as a moisture front crosses strips 208a and 208b. Line A on FIG. 14 corresponds to time point A-A, where the moisture front has progressed partially across conductive strips 208a and 208b. Capacitance is shown to increase to line B and then line C as time points B-B and C-C show further progression across strips 208a and 208b. Finally, line D, where capacitance is shown to level of corresponds to time point D-D, where the moisture front has fully crossed strips 208a and 208b. At point D-D, colorimetric analyte sensing element 130 has been fully saturated with moisture.

As discussed above, system 100 for measuring analyte concentration in an absorbent article uses colorimetric analyte sensing elements 130a, 130b to produce a visual indication of the presence of preselected analytes in samples freshly produced by the wearer of system 100. System 100 also has a means for collecting fluid for later analysis. Holding plate 180 has a fluid collection reservoir 185 attached to holding plate 180 by reservoir connector 183. Fluid collection reservoir 185 may comprise an absorbable material, such as a sponge, to collect bodily fluid, such as urine. The fluid collected by fluid collection reservoir 185 may be sent to a comprehensive testing site to compare the concentrations determined by colorimetric analyte sensing elements 130a, 130b to concentrations determined by "gold standard" test methods. Tests may also be run for other analytes not measured by colorimetric analyte sensing elements 130a, 130b to give a more comprehensive determination of user health.

Figure 11:
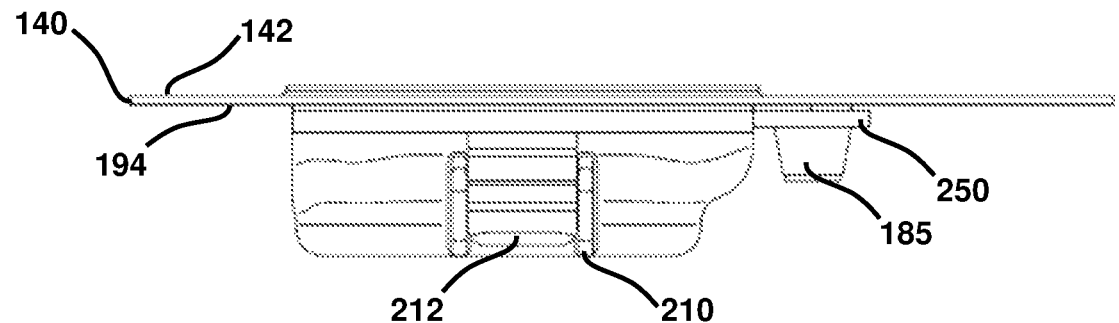
FIG. 11 is a partial side view of the system of FIG. 1.
Figure 12:
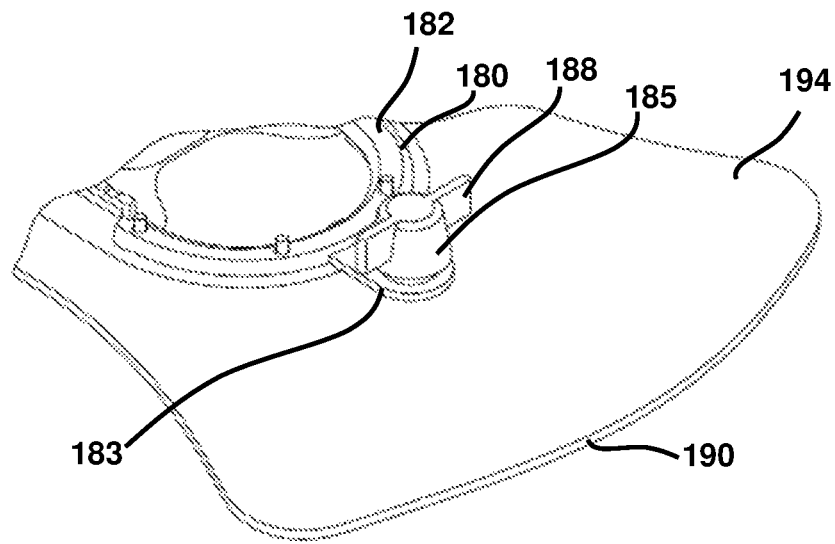
FIG. 12 is a partial bottom perspective view of the indicator component of FIG. 3.

FIGS. 11 and 12 show the connection between durable component 200 and fluid collection reservoir 185. As mentioned above, fluid collection reservoir 185 is attached to holding plate 180 by reservoir connector 183. FIG. 11 is a partial side view of the system 100, while FIG. 12 is a partial top perspective view of the indicator component 120. FIG. 11 shows fluid collection reservoir 185 disposed in opening 252 of reservoir retriever 250. When durable component 200 is detached from holding plate 180, reservoir retriever 250 detaches retrieve fluid collection reservoir 185 from holding plate 180.

FIG. 12 shows holding plate 180 with fluid collection reservoir 185 attached to holding plate 180 by reservoir connector 183. Fluid collection reservoir 185 may have twist-off feature 188 to aid in its removal from bottom side 182 of holding plate 180.

Figure 15:
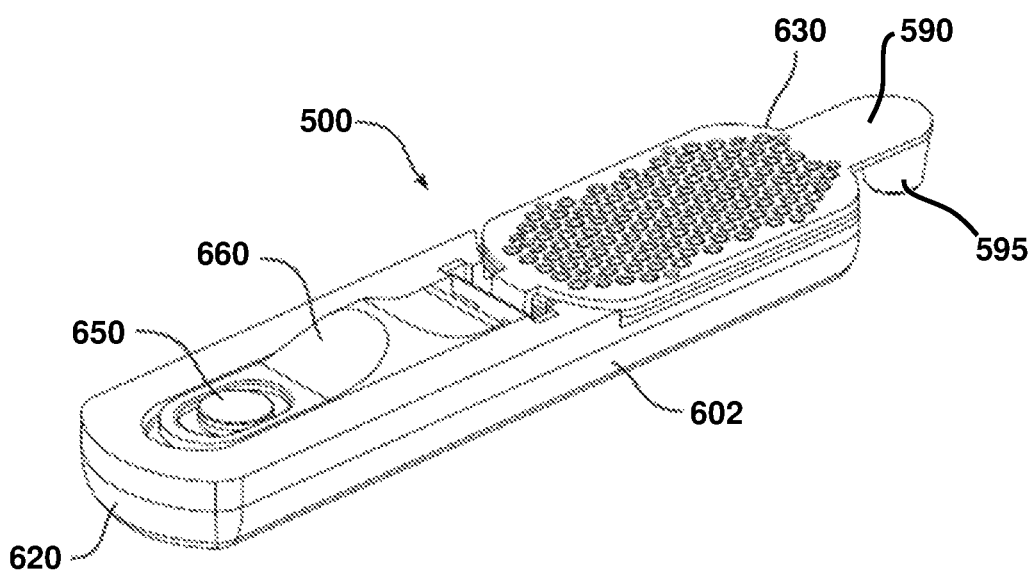
FIG. 15 is a top perspective view of a system for measuring analyte concentration and sample collection in a bodily fluid of the present invention.
Figure 16:
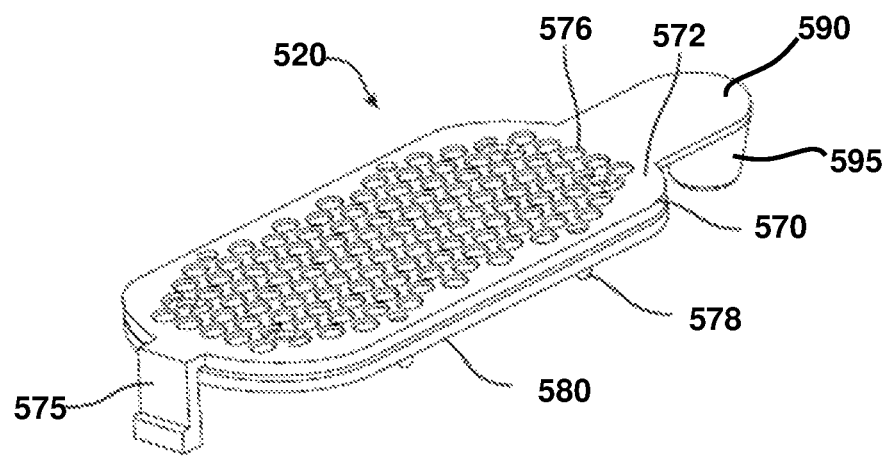
FIG. 16 is a top perspective view of the indicator component and sample collection of the system of FIG. 15.
Figure 17:
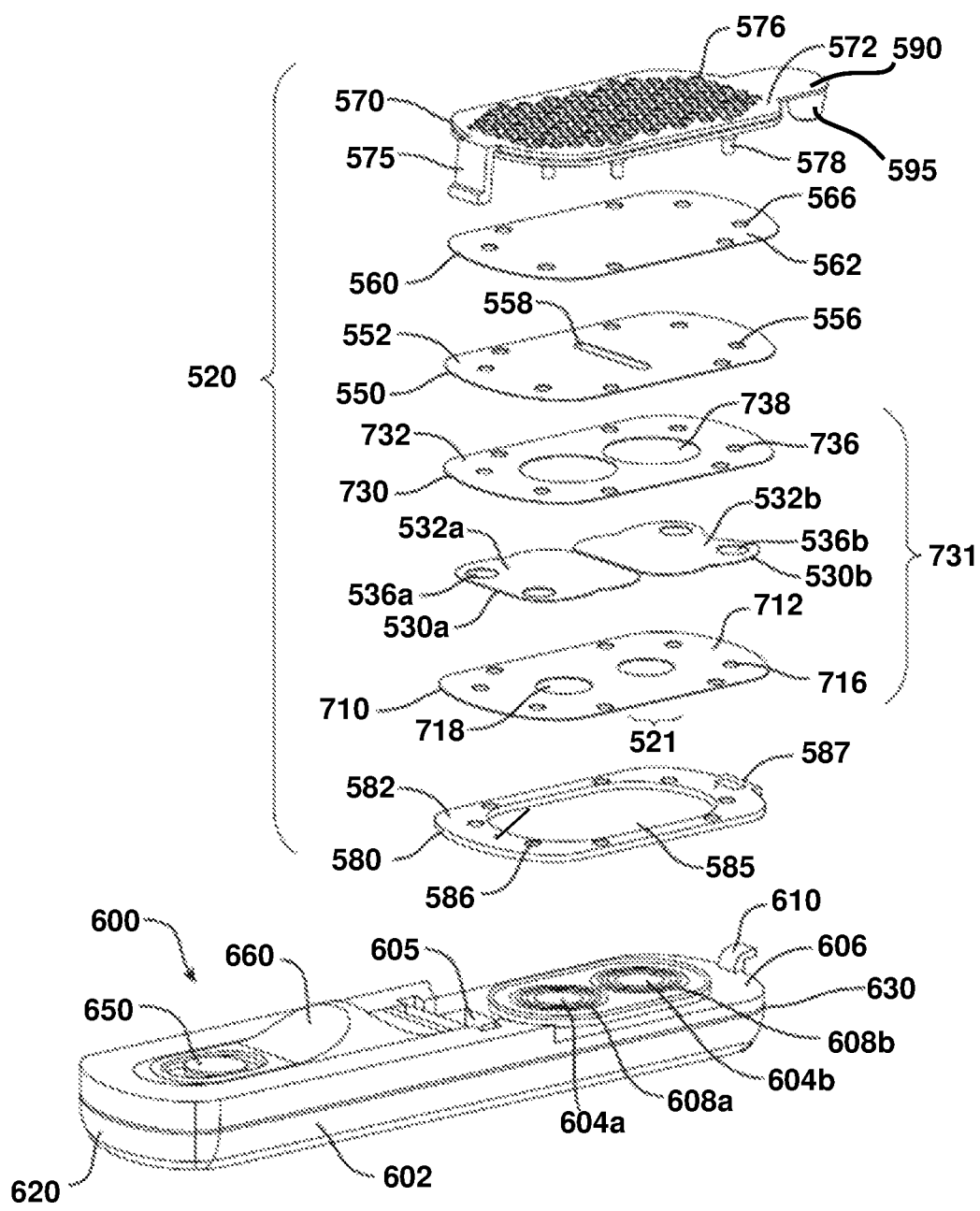
FIG. 17 is a partially exploded view of the indicator component and sample collection system of FIG. 15.

The system for measuring analyte concentrations in bodily fluids may be used in an absorbent article, or it may be directly contacted by bodily fluids outside of an absorbent article. For example, the system can contact bodily fluids collected in a specimen container or may come into contact with bodily fluids such as urine as the fluid is expelled from the human body. FIGS. 15 to 17 show a system for measuring analyte concentration in a bodily fluid of the present invention. System 500 has an indicator component 520 and a durable component 600. FIG. 15 is a top perspective view of system 500 when full assembled. FIG. 16 is a top perspective view of the indicator component 520 of system 500. FIG. 17 is a partially exploded view of system 500, where indicator component 520 is shown in exploded view.

In FIG. 17, indicator component 520 includes an indicator zone 521 is shown to have a pair of colorimetric analyte sensing elements, first colorimetric analyte sensing element 530a, and second colorimetric analyte sensing element 530b. First colorimetric analyte sensing element 530a has a first side 532a and perforations 536a. Second colorimetric analyte sensing element 530b has a first side 532b and perforations 536b.

As discussed before, colorimetric analyte sensing elements 530a, 530b may be reagent impregnated matrices designed to produce a visual indication of the presence of a preselected analyte in sample produced by the user of system 500. The preselected analyte measured by system 500 may be, glucose, ketones, bilirubin, blood, pH, protein, urobilinogen, nitrite, leukocytes, and/or creatinine, among others.

Again, colorimetric analyte sensing elements 530a, 530b may be designed to indicate the presence of the same preselected analyte in sample produced by the user of system 500. In this case, colorimetric analyte sensing elements 530a, 530b act to confirm the analysis. Colorimetric analyte sensing elements 530a, 530b may also be designed to produce a visual indication of the presence of different preselected analytes in sample produced by the user of system 500.

Again, the fluid being tested may be urine and the preselected analyte measured by system 500 is glucose, one or more ketones, or combinations thereof. The presence of higher than normal levels of glucose and/or ketones in the urine and may be due to complications with the user's kidneys, or other conditions such as diabetes mellitus, hyperthyroidism, benign glycosuria, liver cirrhosis, or a high sugar diet.

In addition, choosing appropriate biosensor(s) capable of converting a preferred biomarker into a calorimetrically readable result may be used in genomics, transcriptomics, metabolomics, and proteomics as well to determine the presence of inflammatory biomarkers that are present in urine or other bodily fluids.

The other components of indicator component 520 include a top plate 570, a first flexible web 560, a fluid transport layer 550, a first encapsulation layer 710, a second encapsulation layer 730, and a coupler shown here as holding plate 580.

Colorimetric analyte sensing elements 530a, 530b are encapsulated between first encapsulation layer 710 and second encapsulation layer 730 to form a fluid impervious envelope 731. First encapsulation layer 710 has a first side 712, perforations 716, and apertures 718. Second encapsulation layer 730 has a first side 732, perforations 736, and apertures 738.

When assembled in indicator component 520, perforations 716 of first encapsulation layer 710 are in alignment with perforations 536a, 536b of colorimetric analyte sensing elements 530a, 530b, as well as perforations 736 of second encapsulation layer 730.

In addition, apertures 718 of first encapsulation layer 710 are in alignment with apertures 738 of second encapsulation layer 730.

FIG. 17 also shows fluid transport layer 550 and first flexible web 560. When assembled in indicator component 520, fluid transport layer 550 is disposed on encapsulated colorimetric analyte sensing elements 530a, 530b of indicator component 520 of system 500. Fluid transport layer 550 has first side 552, first perforations 556 and second perforation 558. First flexible web 560 is disposed on fluid transport layer 550, and has a first side 562, and perforations 566, and is made of a non-absorbing apertured film, such as a polyethylene mesh.

When assembled in indicator component 520, colorimetric analyte sensing elements 230a, 230b, which are encapsulated in the fluid impervious envelope 731, are in fluid communication with fluid transport layer 550. Fluid transport layer 550, in turn, is in fluid communication with first flexible web 560.

Fluid transport layer 550 and first flexible web 560 are designed to control the transport of bodily fluids to the colorimetric analyte sensing elements 530a, 530b and to limit cross-contamination of fluids among different colorimetric analyte sensing elements. In use, bodily fluid first contacts first side 562 of first flexible web 560. Since first flexible web 560 is a non-absorbing apertured film, fluid passes through first flexible web 560 and contacts first side 552 of fluid transport layer 550. The fluid then permeates throughout fluid transport layer 550. Finally, the fluid in transport layer 550 passes through apertures 738 of second encapsulation layer 730 to contact the colorimetric analyte sensing elements 530a, 530b. Again, cross-contamination between the two colorimetric analyte sensing elements is eliminated or at least made insignificant and not detectable by means of the fluid barrier defined by the gap in capillarity within the fluid transport layer 550 provided by the second perforation 558.

Sensing elements 530a, 530b, first encapsulation layer 710, second encapsulation layer 730, fluid transport layer 550, and first flexible web 560 are stacked, as shown in FIG. 17, and are held together by top plate 570 and holding plate 580. Top plate 570 has pins 578. Pins 578 sequentially pass through perforations 566 of first flexible web 560, first perforations 556 of fluid transport layer 550, perforations 716 of first encapsulation layer 710, perforations 536a, 536b of colorimetric analyte sensing elements 530a, 530b, perforations 736 of second encapsulation layer 730, and are finally disposed in blind holes 586 on first side 582 of holding plate 580. A friction fit between top plate pins 578 and blind holes 586 hold the components of indicator component 520 together. Alternative assemblies may be held together by other interactions, such as snap fit, ultrasonic weld, heat weld, other mechanical fasteners, and the like.

Top plate 570 has apertures 576 which help direct fluid to first side 562 of first flexible web 560. Top plate 570 also has disposed thereon protrusion 575. Protrusion 575, as well as protrusion 587 disposed on holding plate 580 are means of attaching indicator component 520 to durable component 600 of system 500.

System 500 also has a means for collecting fluid for later analysis. Holding plate 580 has a first side 572, and a fluid collection reservoir 595 attached to top plate 570 by reservoir connector 590. Fluid collection reservoir 595 may comprise an absorbable material, such as a sponge, to collect bodily fluid, such as urine. The fluid collected by fluid collection reservoir 185 may be sent to a comprehensive testing site to compare the concentrations determined by colorimetric analyte sensing elements 530a, 530b to concentrations determined by "gold standard" test methods. Tests may also be run for other analytes not measured by colorimetric analyte sensing elements 530a, 530b to give a more comprehensive determination of user health. Fluid collection reservoir 595 is detached from top plate 570 by snapping reservoir connector 590.

Durable component 600 is shown in top perspective view in FIG. 17. Durable component 600, with proximal end 620 and distal end 630, has a housing 602 with a pair of windows, first window 604a, and second window 604b. Durable component 600 also has a flat top surface 606, conductive strips 608a and 608b, receiving element 605, protrusion 610, activation button 650, and finger grip 660. First window 604a and second window 604b align with aperture 585 of holding plate 580.

Though not shown, a pair of spectrophotometers are disposed in housing 602. The first spectrophotometer is adjacent to and in optical communication with first window 604a, while the second spectrophotometer is adjacent to and in optical communication with second window 604b. The first spectrophotometer is in optical communication with colorimetric analyte sensing element 530a, and the second spectrophotometer is in optical communication with colorimetric analyte sensing element 530b. While the durable component 600 has been shown with two spectrophotometers, additional spectrophotometers may be included for measurements of additional analytes or bodily fluid conditions, such as pH, temperature, etc. Indicator zone 521 is the area of indicator component 520 where colorimetric analyte sensing element 530a is exposed to light source(s).

Thought not shown, durable component 600 also has a printed circuit board (PCB) with a computing system having one or more processors and a memory, as well as means for electronic communication to send the results of analyses to data processing systems that are external to system 500. Data processing systems that may be used include at least one external device including server computers, client computers, and handheld devices such as cellphones.

As discussed elsewhere in the specification, the spectrophotometers may include at least one or more, or two or more, or four or more, or six or more light sources and at least one, or at least two or more photodetectors. Also, as mentioned earlier, light sources in durable component 600 may be light-emitting diodes (LEDs), and more specifically, RGB LEDs. The light sources may sequentially emit red light, green light, and blue light, allowing for the near simultaneous collection of three data points, or, the sequence of emitted red light, green light, and blue light may vary.

Photodetectors in durable component 600 also, as discussed previously, may specifically measure the red, green, and blue light, allowing data to be obtained in narrow wavelength regions, and may be coated with a protective material to reduce the possibility of damage to their components.

FIG. 15 shows a top perspective view of durable component 600 and indicator component 520 assembled to form system 500. Here, indicator component 520 is disposed on distal end 630 of durable component 600. Top plate 570 of durable component 600 has protrusion 575, and holding plate 580 has protrusion 587. Durable component 600 has receiving element 605 and protrusion 610. To releasably attach indicator component 520 to durable component 600, protrusion 575 of top plate 570 is disposed in receiving element 605 of durable component 600. Then, protrusion 587 of holding plate 580 is engaged with protrusion 610 of durable component 600 with a snap connection.

FIG. 17 shows conductive strips 608a and 608b disposed on top surface 606 of durable component 600. Conductive strips 608a and 608b act as a moisture sensor in system 500. They are arranged and configured to communicate the presence of moisture in colorimetric analyte sensing elements 530a, 530b to the computing system disposed in durable component 600. As shown, conductive strips 608a are associated with first window 604a and colorimetric analyte sensing element 530a. Conductive strips 308b are associated with second window 604b and colorimetric analyte sensing element 530b. The computing system disposed in durable component 600 is operatively connected to the moisture sensors as well as the components of the spectrophotometer.

The mode of operation of conductive strips 608a and 608b as moisture sensors are identical to the operation of conductive strips 208a and 208b as described in FIGS. 13 and 14.

The moisture front progresses partially, and finally, fully across conductive strips 608a and 608b.

A durable component may be matched with a plurality of indicator components to create a kit for measuring analyte concentration in an absorbent article comprising. For example, the kit may have a durable component 200 or 600 (described above) and a plurality of indicator components, 120, 520 (also described above). To ensure integrity of the indicator components during storage, each such indicator component is enclosed in an individual package.

The present invention also includes a method of measuring analyte concentration in an absorbent article. Bodily fluid is collected and transported via a transport layer to at least one colorimetric analyte sensing element. The presence of the bodily fluid at the at least one colorimetric analyte sensing element begins a countdown for a predetermined time period. Optical data relating to the colorimetric analyte sensing element is collected by at least one spectrophotometer after the predetermined time period. The optical data is communicated to a computing system having at least one processor and data storage. The optical data is analyzed to determine at least one analyte concentration in the bodily fluid.

The predetermined time period following bodily fluid contact with the colorimetric analyte sensing element could be greater than 15 seconds, or greater than 30 seconds, or greater than 60 seconds, or greater than 120 seconds, or greater than 240 seconds, or greater than 300 seconds, or greater than 360 seconds or more. The predetermined time period following bodily fluid contact with the colorimetric analyte sensing element could be a predetermined time range, for example, from about 15 to about 360 seconds, or from about 30 to about 240 seconds, or from about 120 to about 180 seconds, or from about 240 to about 360 seconds.

The analyte measured by system may be, glucose, ketone, bilirubin, blood, pH, protein, urobilinogen, nitrite, leukocytes, and/or creatinine, among others.

The analytes found in bodily fluids potentially carries evidence of developing metabolic system problems. There is a desire for people in and out of the medical establishment to track and analyze changes in the concentration of analytes in bodily fluids over time. These changes may be useful for predicting risk of a future disease conditions. Therefore, the systems discussed in the present invention allow for a method for predicting risk of a future disease condition.

As above, bodily fluid is collected and transported via a transport layer to at least one colorimetric analyte sensing element. The presence of the bodily fluid at the at least one colorimetric analyte sensing element begins a countdown for a predetermined time period. Optical data relating to the colorimetric analyte sensing element is collected by at least one spectrophotometer after the predetermined time period. The optical data is communicated to a computing system having at least one processor and data storage. The optical data is analyzed to determine at least one analyte concentration in the bodily fluid. A threshold analyte concentration of the at least one analyte concentration that indicates the risk of developing a future disease condition is compared against the at least one analyte concentration, and this can be recorded over time. Thus, the risk of developing a future disease condition may be monitored over time.

The system may be arranged, configured, and programmed with multiple photodetectors 124 and multiple colorimetric analyte sensing elements 30 to determine multiple analyte concentrations in the bodily fluid.

Non-invasively measuring the analyte concentration in bodily fluids is also ideally suited for epidemiological studies to rapidly identify problems prevalent in specific geographies or for specific populations of people. The analyte concentration measurements from system 10 may be collected over a wide population for long periods of time. The collected data may be studied to determine relationship between various analyte levels and disease states or combined with other physiological parameter such as blood pressure, blood oxygen level, and pulse rate, or with vital statistics such as age, sex, weight, and nationality, to create a predictive model of future disease states as a function of the saved parameters.

The foregoing methods may employ a system deployed in or in conjunction with an absorbent article, such as a diaper or pad, or they may employ directly contacting bodily fluids without the use of an absorbent article. For example, system 500 may be attached to a body-facing surface of the diaper. System 500 of FIGS. 15-17 may be directly contacted with bodily fluids. It may be dipped into bodily fluids that are first collected in a specimen container by grasping system 500 by finger grip 660 on proximal end 620 of durable component 600. System 500 may be energized by user engaging activation button 650 on proximal end 620 of durable component 600 before or after placing distal end 630 into specimen container. Alternatively, the indicator component of system 500 may be placed in a stream of bodily fluids such as urine as the fluid is expelled from the human body. In these uses, durable component 600 is a handheld analyzer.

The specification, embodiments, and examples above are presented to aid in the complete and non-limiting understanding of the invention disclosed herein. Since many variations and embodiments of the invention can be made without departing from its spirit and scope, the invention resides in the claims hereinafter appended.

What is claimed is:
1. A system for measuring analyte concentration in a bodily fluid comprising:
  a) a durable component comprising a housing having at least one window and containing:
    i) at least one spectrophotometer adjacent to and optically communicating with the window,
    ii) a computing system having at least one processor and data storage,
    iii) means for electronic communication between the computing system and at least one external device;
  b) an indicator component comprising an indicator zone comprising at least one colorimetric analyte sensing element and a fluid transport layer in fluid communication with the indicator zone;
  c) at least one moisture sensor adjacent to the indicator zone; and
  d) a fluid collection reservoir having fluid impervious walls and a port in fluid communication with the fluid transport layer, the fluid collection reservoir being releasable from at least one of the indicator component and the durable component at a predetermined breaking point;
wherein:
  I) the indicator component is arranged and configured for attachment to the durable component while the indicator zone is disposed adjacent to and in optical communication with the at least one window and the at least one spectrophotometer,
  II) the computing system is operatively connected to the moisture sensor and the at least one spectrophotometer,
  III) the moisture sensor is arranged and configured to communicate the presence of moisture in the colorimetric analyte sensing element to the computing system; and
  IV) each of the at least one colorimetric analyte sensing element is associated with a spectrophotometer, and
  V) the fluid collection reservoir is arranged and configured to provide a fluid transport gradient to draw the bodily fluid thereto and is sealable upon detachment from the indicator component.

2. The system of claim 1 wherein the indicator component comprises at least two colorimetric analyte sensing elements, each of the at least two colorimetric sensing elements being isolated from other colorimetric sensing elements and further comprises a fluid impervious envelope surrounding the indicator zone, the fluid impervious envelope having a discrete pocket arranged on configured to contain each of the at least two colorimetric sensing elements and each pocket has a unique aperture in fluid communication with the fluid transport layer.

3. The system of claim 1 wherein the indicator component further comprises:
  i) a top plate;
  ii) a first flexible web layer;
  iii) a fluid transport layer adjacent the first flexible web layer;
  iv) a fluid impervious envelope surrounding the indicator zone adjacent the fluid transport layer;
  v) a second flexible web layer adjacent the fluid impervious envelope;
  vi) attachment means disposed on the second flexible web layer; and
  vii) a holding plate;
wherein:
  VI) the first flexible web layer, fluid transport layer, fluid impervious envelope, and the second flexible web layer are stacked in order and secured between the top plate and the holding plate;
  VII) the indicator zone comprises at least two colorimetric analyte sensing elements;
  VIII) the fluid impervious envelope has a discrete pocket arranged on configured to contain each of the at least two colorimetric analyte sensing elements and each pocket has a unique aperture in fluid communication with the fluid transport layer;
  IX) the fluid transport layer is arranged and configured to inhibit fluid transport between apertures in the fluid impervious envelope; and
  X) the fluid collection reservoir is releasably attached to the holding plate.

4. The system of claim 1 wherein the fluid collection reservoir further comprises an absorbent structure contained by the fluid impervious walls.

5. The system of claim 1 wherein the indicator component is releasably attached to the durable component.

6. The system of claim 1 arranged and configured for placement into a diaper.

7. A handheld device comprising the system of claim 1.

8. A kit comprising the system of claim 1 and additional indicator components, each indicator component and additional indicator components, each being enclosed in an individual package.

9. A method of measuring analyte concentration in a bodily fluid comprising:
   a) collecting and transporting bodily fluid to at least one colorimetric analyte sensing element and at least one fluid collection reservoir having fluid impervious walls and a port,
   b) detecting the presence of bodily fluid in contact with the at least one colorimetric analyte sensing element,
   c) collecting optical data relating to the at least one colorimetric analyte sensing element with at least one spectrophotometer after a predetermined time period after detecting the presence of bodily fluid in contact with the colorimetric analyte sensing element,
   d) communicating the optical data to a computing system having at least one processor and data storage,
   e) analyzing the optical data to determine at least one analyte concentration in the bodily fluid, and
   f) sealing the fluid collection reservoir for transport of the sealed fluid collection reservoir to a laboratory for laboratory analysis.

10. The method of claim 9 wherein the bodily fluid is urine.

11. The method of claim 10 wherein the analyte is selected from the group consisting of glucose, ketones, bilirubin, blood, protein, urobilinogen, nitrite, leukocytes, and/or creatinine, and combinations thereof.

12. The method of claim 9 further comprising the step of:
   g) instructing the laboratory to analyze the bodily fluid for the at least one analyte and comparing the concentration of the at least one analyte from step e) and the laboratory analysis.

13. The method of claim 9 further comprising the step of:
   x) instructing the laboratory to analyze a panel including a plurality of biomarkers.

14. The method of claim 13 wherein the panel including a plurality of biomarkers includes the at least one analyte.

15. A method of measuring analyte concentration in a bodily fluid comprising:
   a) obtaining a durable component comprising a housing having at least one window and containing:
      i) at least one spectrophotometer adjacent to and optically communicating with the window,
      ii) a computing system having at least one processor and data storage, and
      iii) means for electronic communication between the computing system and at least one external device, and
      iv) at least one moisture sensor;
   b) removing an indicator component from an individual package, the indicator component comprising (i) an indicator zone comprising at least one colorimetric analyte sensing element, (ii) a fluid transport layer in fluid communication with the indicator zone, and (iii) a fluid collection reservoir having fluid impervious walls and a port in fluid communication with the fluid transport layer, the fluid collection reservoir being releasable from the indicator component at a predetermined breaking point;
   c) coupling the indicator component to the durable component to provide an assembled device, wherein:
      I) the indicator zone is disposed adjacent to and in optical communication with the at least one window and the at least one spectrophotometer,
      II) the computing system is operatively connected to the moisture sensor and the at least one spectrophotometer,
      III) the moisture sensor is disposed adjacent the indicator zone, and
      IV) each of the at least one colorimetric analyte sensing element is associated with a spectrophotometer; and
      V) the fluid collection reservoir is arranged and configured to provide a fluid transport gradient to draw the bodily fluid thereto and is sealable upon detachment from the indicator component; and
   d) placing the assembled device in contact with a source of the bodily fluid;
   e) collecting and transporting the bodily fluid to the at least one colorimetric analyte sensing element and the fluid collection reservoir;
   f) detecting the presence of the bodily fluid in contact with the at least one colorimetric analyte sensing element;
   g) collecting optical data relating to the at least one colorimetric analyte sensing element with at least one spectrophotometer after a predetermined time period after detecting the presence of bodily fluid in contact with the colorimetric analyte sensing element;
   h) communicating the optical data to a computing system having at least one processor and data storage;
   i) analyzing the optical data to determine at least one analyte concentration in the bodily fluid;
   j) removing the fluid collection reservoir from the indicator component; and
   k) sealing the fluid collection reservoir port for transport of the sealed fluid collection reservoir to a laboratory for laboratory analysis.

16. The method of claim 15 in which step (d) comprises attaching the assembled device to a body-facing surface of a diaper.

17. The method of claim 15 in which step (d) comprises contacting the assembled device with the bodily fluid.

18. The method of claim 15 further comprising the steps of:
   l) instructing the laboratory to analyze the bodily fluid for the at least one analyte and comparing the concentration of the at least one analyte from step i) and the laboratory analysis.

19. The method of claim 15 further comprising the step of:
   x) instructing the laboratory to analyze a panel including a plurality of biomarkers.

20. The method of claim 19 wherein the panel including a plurality of biomarkers includes the at least one analyte.

* * * * *